United States Patent [19]
Aishima et al.

[11] Patent Number: 4,943,449
[45] Date of Patent: Jul. 24, 1990

[54] MICROCAPSULES AND PROCESS FOR PRODUCING THEM

[75] Inventors: Shizuo Aishima; Yoshito Takahashi; Masaki Kosemura; Masaaki Ohkawara, all of Yokohama, Japan

[73] Assignee: Ohkawara Kakohki Co., Ltd., Kanagawa, Japan

[21] Appl. No.: 91,793

[22] Filed: Sep. 1, 1987

[30] Foreign Application Priority Data

Dec. 15, 1986 [JP] Japan .................................. 61-298366

[51] Int. Cl.$^5$ ............................................. B01J 13/02
[52] U.S. Cl. ............................. 427/213.3; 427/213.31; 428/402.24; 424/498; 424/499; 426/72; 426/805
[58] Field of Search ..................... 427/213.3, 213.35; 428/402.24

[56] References Cited

U.S. PATENT DOCUMENTS

| | | | |
|---|---|---|---|
| 4,102,806 | 7/1978 | Kondo et al. | 252/316 |
| 4,389,330 | 6/1983 | Tice et al. | 427/213.3 |
| 4,675,236 | 6/1987 | Ohkawara et al. | 428/402.24 |

FOREIGN PATENT DOCUMENTS

| | | | |
|---|---|---|---|
| 762422 | 2/1971 | Belgium | 427/213.3 |
| 2031981 | 8/1975 | Japan | 427/213.3 |

Primary Examiner—Matthew A. Thexton
Assistant Examiner—John M. Covert
Attorney, Agent, or Firm—Armstrong, Nikaido, Marmelstein, Kubovcik & Murray

[57] ABSTRACT

Process for producing microcapsules. Wax or a mixture of wax and protein is dissolved in a mixed solvent consisting of an organic solvent and water, the surfaces of particles of a core substance are wetted with the resulting solution at temperatures of 45 deg.C or below to selectively deposit the wax or the mixture of wax and protein on the particle surfaces and allow them to coat the particle surfaces. And then a slurry containing the particles is subjected to a solvent removal treatment.

5 Claims, 4 Drawing Sheets

MICROCAPSULES AND PROCESS FOR PRODUCING THEM

BACKGROUND OF THE INVENTION AND RELATED ART STATEMENT

The present invention relates to microcapsules and a process for producing them. More particularly, the present invention relates to microcapsules and a process for producing, by wax coating or coating with a mixture of wax and protein, microcapsules which are preferably used in feeds, [particularly, feeds for fries,] medicines, foods, chemical products, etc.

As described in "Technique for Surface Modification of Fine powder by Encapsulation", pages 547 to 551 (particularly page 548) of Chemical Engineering, Vol 46, No. 10 (1982), it is conventionally known that there are 14 processes for producing microcapsules, such as the interfacial polymerization process, the in-liquid drying process and the like.

The microcapsules produced according to these processes are being used in many industrial fields to prepare foods, medicines, agricultural chemicals, feeds, spices, enzymes, active carbon and the like, as described in the above literature. Of the above 14 processes, there are known, as typical processes for coating particles of a core substance with a wax, a suspension-in-gas process (a coating-in-fluid-layer process) and a melting-dispersion-cooling process (a pelletization process by spraying and solidification).

However, the above mentioned processes have defects in that degradation of the core substance particles tends to occur, that the film formed on the particles becomes scaly and no uniform film is formed, and that a large amount of a wax is required to obtain a complete film on the particles.

U.S. Pat. No. 4,675,236 discloses mono-core type microcapsules and a process for producing them.

The patent relates to wax-coated microcapsules in which the wax coating is prepared by once melting the wax particles over the surface of the core particles and then resolidifying them.

On the other hand, at present, microcapsules and a process for producing them by simultaneously coating hydrophobic waxes (in particular, lipids) and hydrophilic proteins are not known in the field.

An object of the present invention is to provide microcapsules and a process for producing them to solve the above mentioned defects associated with the conventional processes.

Another object of the present invention is to provide microcapsules and a process for producing them on which waxes or a mixture of waxes and proteins are coated uniformly.

SUMMARY OF THE INVENTION

According to the present invention, there are provided microcapsules comprising particles of from 5 $\mu$m to 5 mm in size on the surface of which waxes or a mixture of wax and protein have been coated as a layer of from 0.1 to 10 $\mu$m in thickness. Further, there is provided a process for producing microcapsules by wax coating or coating with a mixture of wax and protein, which comprises dissolving at least one wax or a mixture of wax and protein in a mixed solvent consisting of an organic solvent and water, immersing particles of a core substance in the resulting solution to selectively deposit the wax or the mixture of wax and protein on the surfaces of the core substance particles, allowing the wax or the mixture of wax and protein to coat the particle surfaces, and then subjecting a slurry containing the coated particles to a solvent removal treatment.

DETAILED DESCRIPTION OF THE INVENTION

Figure 1:
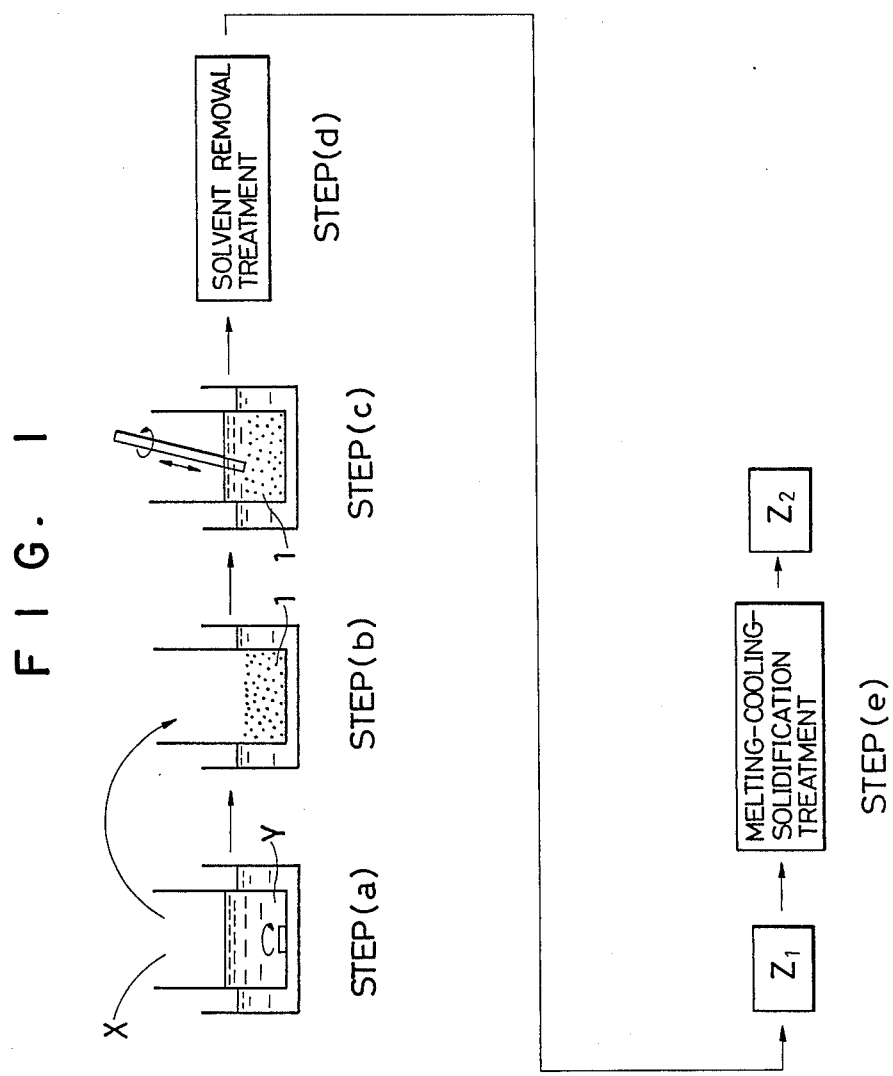
FIG. 1 is a flow chart showing a typical embodiment of the present process.

The organic solvent used in the present invention can be any as long as it is miscible with water and can dissolve the wax or the mixture of wax and protein used in the present invention, as mentioned above. The organic solvent is preferably selected from methanol, ethanol, propanol, acetone and methyl ethyl ketone, which are all polar solvents. Of these, ethanol and acetone are particularly preferred.

The concentration of the organic solvent in the mixed solvent is ordinarily 65 to 95% by volume. It is decided in view of the type of wax and/or protein used and the amount of wax and/or protein required. The concentration of the organic solvent is, for example, 65 to 85% by volume, preferably 75 to 80% by volume in the case of methanol; 70 to 95% by volume, preferably 75 to 90% by volume in the case of ethanol; 80 to 95% by volume, preferably 85 to 90% by volume in the case of propanol; 70 to 95% by volume, preferably 75 to 90% by volume in the case of acetone; and 80 to 95% by volume, preferably 85 to 90% by volume in the case of methyl ethyl ketone. When the concentration of the organic solvent is lower than 65% by volume, the solubility of the wax decreases remarkably and it is necessary to increase the solution temperature to higher than 45 deg. C. When the concentration exceeds 95% by volume, the selective deposition of the wax and protein on the particle surfaces becomes difficult.

Furthermore, production of microcapsules of a more-core type or a multi-core type can be adjusted by selecting the concentration of the organic solvent in the mixed solvent. In case that the concentration of the organic solvent in the mixed solvent is raised within said range, microcapsules of a mono-core type are produced. On the other hand, when the concentration is lowered, microcapsules of a multi-core type are produced.

To be concrete, the concentration of the organic solvent in the mixed solvent is 80 to 95% by volume, preferably 80 to 90% by volume when producing mono-core type microcapsules. The concentration of the organic solvent is 65 to 85% by volume, preferably 70 to 80% by volume when producing multi-core microcapsules.

The operation of wetting the particle surfaces with the mixed solvent containing a wax is conducted at temperatures of 45 deg. C or below, ordinarily at 20 deg. C to 40 deg. C. When it is conducted at temperatures higher than 45 deg. C, it causes degradation of the core substance.

In the microcapsules of the present invention, the core substance particles can be an organic substance or an inorganic substance. It is preferable that these substances contain a water-soluble substance. Examples of the organic substance include not only those shown in Examples 1 to 4 which appear later, but also particles of foods, seasonings, medicines, additives for medicine, spices, enzymes, feeds, etc. Examples of the inorganic substance include particles of oxide ceramics, non-oxide ceramics, inorganic salts, active carbon, zeolite, etc.

These core substance particles have particle diameters of 5 $\mu$m to 5 mm, preferably 5 to 500 $\mu$m. Preferably, they have a spherical shape or a shape close to it.

As the wax, there are used those soluble in organic solvents. Specific examples include the followings.

(1) Fatty acids

Saturated fatty acids of carbon numbers 10 to 20 ($C_{10} \sim C_{20}$) and
Unsaturated fatty acids of carbon numbers 18 to 24 ($C_{18} \sim C_{24}$).

EXAMPLE

Capric acid, undecanoic acid, lauric acid, tridecylic acid, myristic acid, palmitic acid, stearic acid, elaidic acid, nonadecanoic acid, arachic acid, behenic acid, lignoceric acid, octadecenoic acid, vaccenic acid, erucic acid, brassidic acid, cerotic acid, montanic acid, hexadecenoic acid, eicosenoic acid, pentadecylic acid, heptadecylic acid, heptacosanoic acid, melissic acid, lacceric acid, undecylenic acid, cetoleic acid, arachidonic acid, octadecynoic acid, etc.

(2) Higher alcohols

Higher alcohols of carbon numbers 10 to 20 ($C_{10} \sim C_{20}$)

EXAMPLE

Undecanol, lauryl alcohol, tridecyl alcohol, myristyl alcohol, cetyl alcohol, stearyl alcohol, elaidic alcohol, nonadecyl alcohol, eicosyl alcohol, ceryl alcohol, pentadecyl alcohol, heptadecyl alcohol, melissyl alcohol, laccerol, undecyl alcohol, etc.

(3) Fatty acid glycerides

Mono-, di-, and tri-glycerine esters of higher fatty acids of carbon numbers 10 to 24 ($C_{10} \sim C_{24}$).

EXAMPLE

Palmitin, stearin, myristin, laurin.

(4) Others

Sterols (cholesterol and their derivatives)
Phospholipids (lecithin)
These waxes can be used singly or in combination, or used in a mixture with the protein.

In case of using the mixture of wax and protein, the amount of the wax to be used is generally from 1 to 30% by weight, preferably from 2 to 10% by weight, based on 100% by weight of the core substance particle.

As the protein, gliadin (wheat) belonging to the prolamin, hordenine (barley), zein (corn), etc. among the simple proteins, are used. The amount of the protein to be used is generally from 0.5 to 8% by weight, preferably from 1 to 3% by weight, to 100% by weight of the core substance particle.

As necessary, a water-soluble substance can be added to the wax or the mixture of wax and protein in order to control the collapse time of microcapsule film. Therefore, it is desirable that the type and amount of the water-soluble substance added be selected in view of the length of time of microcapsule use.

As the water-soluble substance which can be added, there can be mentioned gelatin, gum arabi, sodium carboxymethylcellulose, polyvinyl alcohol (PVA), cellulose acetate phthalate (CAP), Eudragit L30D-55 (brand name, methyl methacrylate—methacrylic acid copolymer), etc.

The microcapsules produced by depositing the wax or the mixture of wax and protein on the particle surfaces to coat the surfaces with the wax or the mixture of wax and protein are then subjected to a solvent removal treatment to obtain microcapsules of the present invention.

The solvent removal treatment can be easily conducted according to a known treatment method such as spray drying, a combination of vacuum drying and disintegration, or the like.

The process of the present invention exhibits the following surprising phenomena.

In the conventional processes for microcapsule production, it is necessary to completely disperse particles of a core substance in order to obtain microcapsules which are separate from each other and not adherent to each other. In the present invention, however, such mono-core microcapsules can be easily obtained simply by wetting the surfaces of core substance particles with a wax solution or a solution of wax and protein, without the necessity of dispersing the particles. If desired, multi-core microcapsules can also be easily obtained.

Further in the present invention, the total amount of the wax or the mixture of wax and protein used is deposited on the surfaces of the core substance and the deposition of wax or the mixture of wax and protein occurs even between the particles which are sticking to each other. Therefore, when the wax-coated particles or the particles coated by the mixture of wax and protein are disintegrated after the solvent removal treatment, each microcapsule can be obtained independently without causing any breakage of wax film or film of the mixture of wax and protein.

Because of the above phenomena, the thickness of the film can be controlled easily in the process of the present invention. The average thickness t of the film is given by the following equation, based on assumptions that the total amount of the wax or the mixture of wax and protein used adhere to the core substance particles and the particles have a spherical shape.

$$t = (R \cdot \rho_p / 600 \cdot (1-\epsilon) \cdot \rho_w) \times d_{50} \ (\mu m)$$

wherein
$R$ = weight ratio of wax or mixture of wax and protein to core substance, (%)
$\rho_p$ = density of particles, (g/cc)
$\rho_w$ = density of wax or mixture of wax and protein, (g/cc)
$d_{50}$ = average diameter of core substance, ($\mu$m)
$\epsilon$ = void of wax or mixture of wax and protein, (—)

The film thickness t can be easily obtained from the above equation.

The microcapsules produced according to the present process can further be subjected to a post-treatment, namely, a melting-cooling-solidification treatment, whereby microcapsules having a more dense surface can be obtained.

In one example of the melting-cooling-solidification treatment, only the surface wax of the microcapsules produced according to the present process is momentarily melted with hot air in order not to cause the thermal degradation of the core substance and then cooled with cold air for solidification.

In another example, the microcapsules are melted by a frictional heat in a vessel equipped with a high speed stirrer and then cooled for solidification.

The microcapsules obtained as mentioned above, are particles of from 5 $\mu$m to 5 mm in size on which waxes or a mixture of wax and protein are coated as a layer of 0.1 to 10 $\mu$m in thickness on the surface of the core substance particles.

EXAMPLES

The present invention will be explained in more detail by referring to Examples. However, it is apparent that the present invention is not restricted to these Examples.

EXAMPLE 1

Explanation is made by referring to FIG. 1 showing a typical flow chart of the present process.

A mixture X consisting of 3 g of palmitic acid and 2 g of lauric acid was dissolved in a mixed solvent Y consisting of 85 ml of ethanol and 15 ml of water, at 40 deg. C [step (a)]. The resulting solution was poured on 100 g of feed particles 1 of purified casein (particle diameters: 105 to 250 $\mu$m) heated to 40 deg. C on a hot water bath, to immerse the particles 1 in the solution [step (b)]. Promptly, stirring was initiated to make the whole system uniform, and the wax was deposited on the particles 1. In this case, the wax-coated particles caused agglomeration but the agglomerated microcapsules were disintegrated by the stirring [step (c)].

Next, the slurry containing the wax-coated particles was subjected to a solvent removal treatment (vacuum drying under conditions of 20 Torr ×1 hour and 1 Torr×12 hours in this order) [step (d)], and the product was subsequently disintegrated softly to obtain microcapsules Z, of 30 deg. C which are not adherent to each other.

Figure 2:
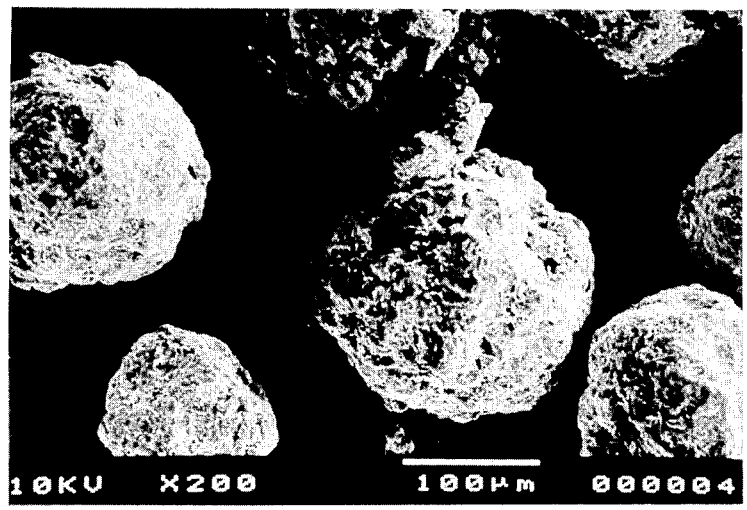
FIG. 2 is a photograph by scanning type electron microscope showing the structure of the microcapsules obtained in Example 1.

The structure of the microcapsules Z, is shown in FIG. 2 of a photograph by scanning type electron microscope. It is seen from FIG. 2 that the wax is uniformly coated on the particle surfaces.

The microcapsules Z, were subjected to a melting-cooling-solidification treatment (hot air temperature 220 deg. C, cold air temperature 20 deg. C, exhaust gas temperature 50 deg. C [step (e)] to obtain microcapsules $Z_2$ with a more dense surface which are not adherent to each other.

Figure 3:
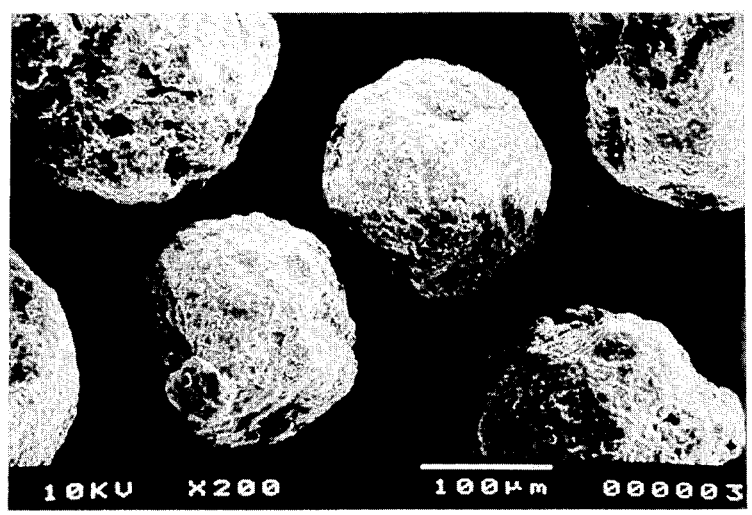
FIG. 3 is a photograph by scanning type electron microscope showing the structure of the microcapsules after melting-cooling-solidification treatment, obtained in Example 1.

The structure of the microcapsules $Z_2$ is shown in FIG. 3 of a photograph by scanning type electron microscope.

EXAMPLE 2

This Example is conducted in the same manner of FIG. 1.

A mixture consisting of 6 g of palmitic acid, 4 g of lauric acid and 4 g of zein was dissolved in a mixed solvent consisting of 255 ml of ethanol and 45 ml of water, at 40 deg. C. The resulting solution was poured on 100 g of particles of a water-soluble vitamin mixture (particle diameters: 10 to 30 $\mu$m) heated to 40 deg. C on a hot water bath, to immerse the particles in the solution. Promptly, stirring was initiated to make the whole system uniform.

Next, the slurry containing the particles was subjected to a solvent removal treatment (spray drying at an inlet temperature of 70 deg. C and an outlet temperature of 50 deg. C) [step (d)], to obtain microcapsules of 30 deg. C which are not adherent to each other.

Figure 4:
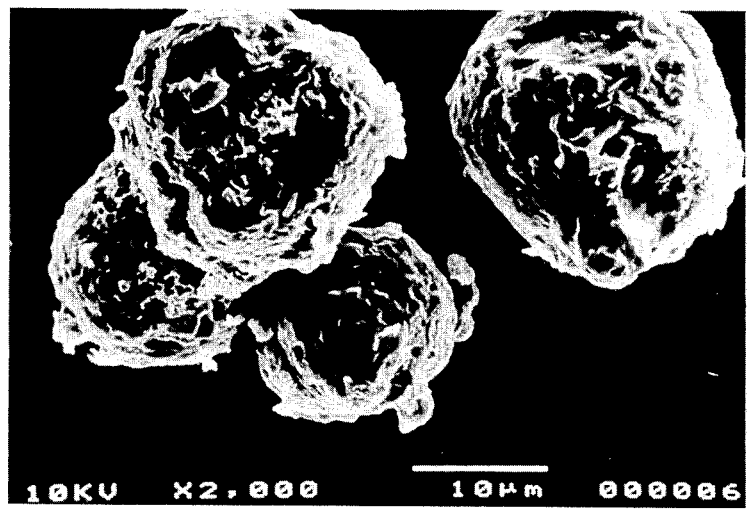
FIGS. 4 to 6 are photographs by scanning type electron microscope showing the structures of the microcapsules obtained in Examples 2 to 4, respectively.

The structure of the microcapsules obtained is shown in FIG. 4 of a photograph by scanning type electron microscope.

EXAMPLE 3

Microcapsules were produced in the same manner as in Example 1 except that there were used, as a wax, a mixture consisting of 2.5 g of stearic acid and 2.5 g of lauric acid, and as a solvent, a mixed solvent consisting of 90 ml of ethanol and 10 ml of water, and as core substance, 100 g of particles of a mixture of an agricultural chemical and lactose, having particle diameters of 44 to 63 $\mu$m.

Figure 5:
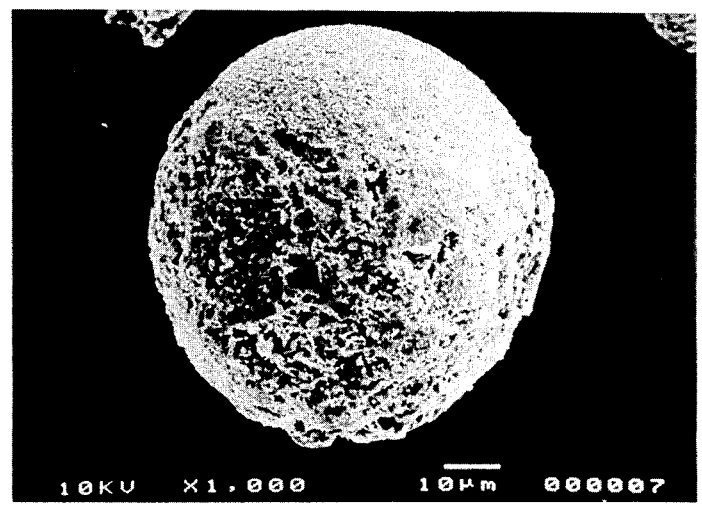

The structure of the microcapsules obtained is shown in FIG. 5 of a photograph by scanning type electron microscope.

EXAMPLE 4

Microcapsules were produced in the same manner as in Example 1 except that there were used, as a wax, a mixture consisting of 3 g of palmitic acid and 2 g of capric acid, and as a solvent, a mixed solvent consisting of 80 ml of ethanol and 20 ml of water, and as a core substance, 100 g of particles formed from 90% by weight of a mineral mixture and 10% by weight of dextrin, having particle diameters of 63 to 105 $\mu$m.

Figure 6:
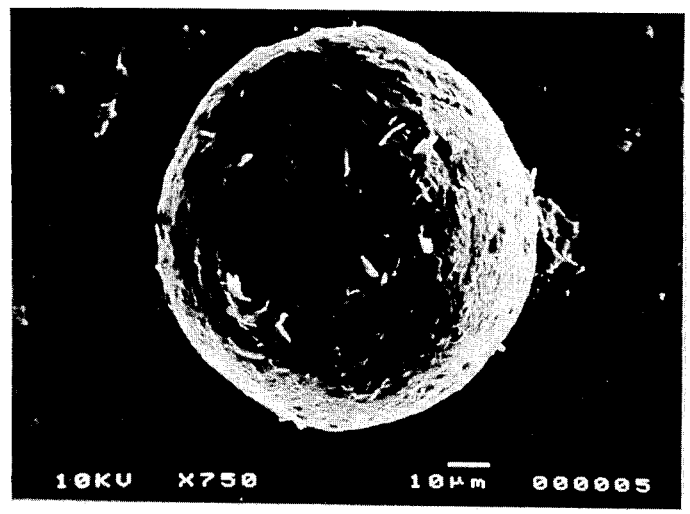

The structure of the microcapsules obtained is shown in FIG. 6 of a photograph by scanning type electron microscope.

According to the present process for producing microcapsules, there can be coated on core substance particles of any size without causing the thermal denaturation of the core substance.

What is claimed is:

1. A process for producing microcapsules which comprises dissolving wax or a mixture of wax and protein in a mixed solvent consisting of 65 to 90% by volume of an organic solvent miscible with water, and water, wetting, with the resulting solution, the surfaces of particles of a core substance at a temperature of 45° C. or below to selectively deposit the wax or the mixture of wax and protein on the surfaces of said particles and coat the surfaces of the particles by forming a slurry of the particles of the core substance in said solution; and then subjecting the slurry containing the particles to a solvent removal treatment.

2. A process according to claim 1, wherein the organic solvent is a polar solvent which is miscible with water.

3. A process according to claim 2, wherein the polar solvent is methanol, ethanol, propanol, acetone or methyl ethyl ketone.

4. A process according to claim 1, wherein the concentration of the organic solvent in the mixed solvent is at least 75% by volume.

5. A process according to claim 1, wherein the core substance particles contain a water-soluble substance.

* * * * *